United States Patent [19]
Murui et al.

[11] 4,423,031
[45] Dec. 27, 1983

[54] EYE MAKEUP PREPARATION

[75] Inventors: Yukio Murui; Masaaki Saitoh, both of Yokohama, Japan

[73] Assignee: Shiseido Company, Ltd., Japan

[21] Appl. No.: 288,506

[22] Filed: Jul. 30, 1981

Related U.S. Application Data

[63] Continuation of Ser. No. 92,267, Nov. 8, 1979, abandoned.

[51] Int. Cl.$^3$ ............... A61K 7/021; A61K 31/74; A61K 31/78; A61K 31/00
[52] U.S. Cl. ............................. 424/63; 424/78; 424/81; 424/168
[58] Field of Search ................... 424/63, 78, 81

[56] References Cited

U.S. PATENT DOCUMENTS 3,574,822  4/1971  Shepherd et al. ............... 424/63
3,697,643  10/1972  Shepherd ............................ 424/63

FOREIGN PATENT DOCUMENTS 1952721  9/1970  Fed. Rep. of Germany ........ 424/63
52-27695  7/1977  Japan ................................... 424/63

OTHER PUBLICATIONS

Harrow, Amer. Perf. & Cosm., 4/1971, pp. 51 & 52.

*Primary Examiner*—Dale R. Ore
*Attorney, Agent, or Firm*—Austin R. Miller

[57] ABSTRACT

Liquid or paste eye makeup preparations containing, as a film forming agent, an aqueous emulsion of at least one copolymer of one or more alkyl acrylates having from $C_4$ to $C_{18}$ alkyl groups in the ester portion and one or more alkyl methacrylates having from $C_1$ to $C_4$ alkyl groups in the ester portion is provided. This copolymer emulsion can be advantageously incorporated into eye makeup preparations, such as an eye liner and mascara, to formulate the water resistant, rub-proof and stain-proof liquid or paste eye makeup preparation.

11 Claims, No Drawings

EYE MAKEUP PREPARATION

This is a continuation of application Ser. No. 092,267, filed Nov. 8, 1979, now abandoned.

FIELD OF THE INVENTION

The present invention relates to aqueous liquid or paste type eye makeup preparations, such as eye liner and mascara. More specifically, it relates to water-resistant, rub-proof, stain-proof and smear-proof aqueous liquid or paste type eye makeup preparations containing, as a film-forming constituent, an aqueous emulsion of at least one copolymer of one or more alkyl acrylates having from $C_4$ to $C_{18}$ alkyl groups in the ester portion and one or more alkyl methacrylates having from $C_1$ to $C_4$ alkyl groups in the ester portion.

DESCRIPTION OF THE PRIOR ART

Makeup preparations, especially eye makeup preparations, are typically classified into water-based type, oil-based type and powder type preparations. It is especially important that makeup preparations last for a long time when they are applied, and further, that they be easy to use, be attractive when applied, have good storability and be non-toxic to the skin.

Conventional makeup preparations are subjected to staining and smearing by, for example: human secretions, such as sweat, tears, sebum and the like; moisture, such as rain, snow, water in swimming pools, sea-water and the like; a physical action, such as rubbing with the hands or clothes, and; interaction with other cosmetics. Although these staining and smearing problems have been somewhat solved in oily type and water in oil emulsion type eye makeup preparations (see Japanese Patent Publication No. 52-27695/1977 and Japanese Patent Laid-Open Application No. 52-90637/1977), a satisfactory solution has not been found for aqueous and film forming type eye makeup preparations or other aqueous type eye makeup preparations. For instance, since aqueous type eye makeup preparations contain a large amount of a hydrophilic substance or substances, they are subject to staining and smearing by tears, sweat, rain and the like, that is, they have a poor water-resistant property. On the other hand, the conventional oily type eye makeup preparations are subject to staining and smearing by interaction with human sebum and other cosmetics, that is, they have a poor oil-resistant property. Further, the conventional emulsion type eye makeup preparations have neither a sufficient water-resistant property nor a sufficient oil-resistant property.

The staining and smearing of the conventional makeup preparations are caused not only by water and/or oil, but also, by the movement of the human skin and rubbing with the hand or clothes. In order to prevent the smearing of the eye makeup preparations good adhesion property is one of the important characteristics of eye makeup preparations.

In order to produce an aqueous type eye makeup preparation having good water-resistant, rub-proof and stain-proof properties, various eye makeup preparations have been proposed. However, an aqueous type eye makeup preparation having the desired water-resistant, rub-proof and stain-proof properties has not yet been developed.

Among the aqueous type eye makeup preparations, film-forming type eye makeup preparations containing a polymer emulsion or emulsions are widely used because they are easy to use and they provide good finishing effects. These preparations contain, as a film-forming agent, natural rubber latices, water-soluble polymers, or polymer emulsions derived from an emulsion polymerization using an emulsifying agent. However, since these polymeric substances inherently have a poor water-resistant property, eye makeup preparations having a good water-resistant property cannot be obtained therefrom.

In order to solve the aforementioned water-resistant problem in the conventional eye makeup preparations, emulsion type film-forming eye makeup preparations, such as solid, semi-solid and liquid type makeup preparations for eyelashes (oil-water-polymer emulsion type) have been proposed in, for example, Japanese Patent Publication No. 52-43894/1977. However, since the polymer emulsion itself does not have a good water-resistant property, the water-resistant property of the eye makeup preparations is still not as good as desired.

U.S. Pat. No. 3,639,572 and British Pat. No. 1,110,240 disclose water-resistant, rub-proof and stain-proof cosmetic compositions for application to the skin of the eyelids containing, for example, polymer emulsions of ethyl acrylate (and butyl acrylate), methyl methacrylate (and butyl methacrylate) and methacrylic acid (or itacomic acid). However, the present inventors have found that relatively large amount of ethyl acrylate and methacrylic acid components contained these polymer emulsions impart only a poor water-resistant property to the films obtained from these polymer emulsions, so that the water-resistant property of the proposed cosmetic composition is not as good as desired. In addition, since the amount of the polymer emulsions incorporated into the cosmetic compositions is relatively small (that is, 3 to 7% W/V based on the cosmetic compositions), only an insignificant improvement of the water-resistant property of the eye makeup preparations can be expected.

SUMMARY OF THE INVENTION

The objects of the present invention are to obviate the above-mentioned problems of the conventional aqueous type eye makeup preparations and to provide a water-resistant, stain-proof and rub-proof eye makeup preparation.

Other objects and advantages of the present invention will be apparent from the following description.

In accordance with the present invention, there is provided an eye makeup preparation comprising, as a film-forming constituent, an aqueous emulsion of at least one copolymer of one or more alkyl acrylates having from $C_4$ to $C_{18}$ alkyl groups in the ester portion and one or more alkyl methacrylates having from $C_1$ to $C_4$ alkyl groups in the ester portion.

DESCRIPTION OF THE PREFERRED EMBODIMENT

The present inventors have found that the above-mentioned problems of the conventional aqueous type eye makeup preparations can be solved by the use of the special copolymer emulsion of one or more of said alkyl acrylates and one or more of said alkyl methacrylates, and that the aqueous liquid or paste type eye makeup preparation having outstanding water resistant, stain-proof and rub-proof properties can be provided.

Polymer emulsions having a high water-resistant property used in cosmetic compositions must have all of the following three characteristics, which are different from those used in adhesives and coating compositions.
1. The polymer emulsions should not contain a component which is toxic or harmful to the human body (e.g. non-polymerized toxic monomers and the like).
2. The polymer emulsions should not be affected by microorganisms.
3. The polymer emulsions should have outstanding film-forming characteristics.
   (i) Continuous films should be formed.
   (ii) The films thus formed should be approximately hard and flexible.
   (iii) The films should have an excellent adhesive to human skin or other portions.
   (iv) The films should have an outstanding water-resistant property.

The present inventors have found that the above mentioned characteristics are satisfied by the aqueous copolymer emulsion of one or more alkyl acrylates having from $C_4$ to $C_{18}$ alkyl groups, preferably from $C_4$ to $C_8$ alkyl groups, in the ester portion, and one or more alkyl methacrylates having from $C_1$ to $C_4$ groups in the ester portion.

The alkyl acrylates used in the present invention include, for example, butyl acrylate (BA), isobutyl acrylate (IBA), hexyl acrylates (HA), 2-ethylhexyl acrylate (2EHA) and the like. The use of 2-ethylhexyl acrylate or mixtures thereof with the other alkyl acrylates having from $C_4$ to $C_8$ alkyl groups is most preferable. In the case where the carbon atoms of the alkyl ester portion of the alkyl acrylate which is used alone or together with the other alkyl acrylates are 3 or less, the water-resistant property of the copolymer films becomes poor, so that good eye makeup preparations cannot be obtained when such copolymer emulsion is incorporated into the eye makeup preparations. Contrary to this, in the case where there are 19 or more carbon atoms in the alkyl ester portion of the alkyl acrylate, the reactivity of the alkyl acrylates in an emulsion polymerization is unpreferably low. Since a copolymer emulsion containing alkyl acrylates having $C_9$ or more alkyl groups in the ester portion has an unpleasant odor (the removal of odor tends to be difficult when the molecular weight of the monomer becomes large), the incorporation of such copolymer emulsion into the makeup preparations is somewhat limited.

Alkyl methacrylates used, together with said alkyl acrylates, in the production of the aqueous copolymer emulsion of the present invention include those which have a minimum film-forming temperature (MFT) (represented by a glass transition temperature Tg) of 0° C. or more when they are polymerized alone. Examples of such alkyl methacrylates are methyl methacrylate (MMA), ethyl methacrylate (EMA), butyl methacrylate (BMA) and the like. Other comonomers which are copolymerizable with said alkyl acrylates and homopolymers which have a MFT (Tg) of 0° C. or more may be used, together with said alkyl acrylates, in the production of the aqueous emulsion of the present invention. However, vinyl acetate, styrene, acrylonitrile, vinyl chloride and the like should not be used, as comonomers, due to their toxicity, their poor, water-resistant properties and/or bad odor.

The copolymerization ratio of the alkyl acrylates to the alkyl methacrylates may be varied depending on the kinds of acrylates and methacrylates, the types of eye makeup preparations, the kinds and amounts of the other components incorporated into the eye makeup preparations (e.g. pigments, oils). However, generally speaking, the preferable ratio (by weight) of the alkyl acrylates to the alkyl methacrylates is within the range of from 3/7 to 8/2 and, more preferably, the range of from 5/5 to 7/3. This range approximately corresponds to the range of a MFT (Tg) of the copolymer of from 30° C. to −35° C., and, more preferably, of from 10° C. to −10° C. The solid content of the aqueous solid copolymer emulsions is preferably within the range of from 20 to 50% by weight, based on the total weight of the eye makeup preparation. The preferable content of the solid copolymer in the preparation is within the range of from 10 to 25% by weight.

The above-mentioned aqueous emulsions can be prepared according to any conventional emulsion polymerization techniques. For instance, an aqueous solution of an emulsifying agent is first charged into a polymerization reactor, and then, monomers, and a polymerization initiator or initiators (e.g. hydrogen peroxide, ammonium persulfate or the like) are dropwise added over several hours at an elevated temperature such as 50° to 80° C. After the completion of the addition, the polymerization is continued for a period of time, and then, the unreacted monomer is removed under a reduced pressure. As the emulsifying agent, anionic emulsifying agents and nonionic emulsifying agents can be preferably used in an amount of, for example, from 0.2 to 5% by weight. Although the amount of the polymerization initiator(s) may be varied over a wide range, the amount of the polymerization initiator(s) is usually within the range of from 0.05 to 1.0% by by weight. A small amount of carboxy-containing monomers (e.g. acrylic acids, methacrylic acids) may be optionally used, as comonomers, in addition to the alkyl acrylates and the alkyl methacrylates.

An aqueous dispersion type eye makeup preparation according to the present invention contains, as main constituents, from 20 to 50% by weight of an aqueous emulsion of at least one copolymer of one or more alkyl acrylates having from $C_4$ to $C_{18}$ alkyl groups in the ester portion and one or more alkyl methacrylates having from $C_1$ to $C_4$ alkyl groups, from 1 to 10% by weight of at least one humectant, from 5 to 30% by weight of at least one pharmaceutically acceptable finely divided inorganic pigment, from 0.1 to 5% by weight of at least one surface active agent, from 0.1 to 3% by weight of at least one thickener, from 0.5 to 5% by weight of at least one plasticizer and a balance of water. The content of the solid copolymer in the preparation is preferably within the range of from 10 to 25% by weight.

An O/W (oil in water) emulsion type eye makeup preparation according to the present invention contains, as main constituents, from 20 to 50% by weight of an aqueous emulsion of at least one copolymer of one or more alkyl acrylates having from $C_4$ to $C_{18}$ alkyl groups in the ester portion and one or more alkyl methacrylates having from $C_1$ to $C_4$ alkyl groups in the ester portion, from 1 to 30% by weight of at least one member selected from waxes, fats and oils, from 1 to 10% by weight of at least one humectant, from 5 to 30% by weight of at least one pharmaceutically acceptable finely divided inorganic pigment, from 0.1 to 6% by weight of at least one surface active agent, from 0.1 to 3% by weight of at least one thickener and from 20 to 50% by weight of water. The content of the solid copolymer in the preparation is preferably within the range of from 10 to 25% by weight.

An S/W/O paste type eye makeup preparation according to the present invention contains, as main constituents, from 5 to 50% by weight of an aqueous emulsion of at least one copolymer of one or more alkyl acrylates having from $C_4$ to $C_{18}$ alkyl groups in the ester portion and one or more alkyl methacrylates having from $C_1$ to $C_4$ alkyl groups in the ester portion, from 5 to 30% by weight of at least one member selected from waxes and fats, from 20 to 60% by weight of at least one volatile branched hydrocarbon, from 3 to 30% by weight of at least one pharmaceutically acceptable finely divided inorganic pigment and from 1 to 5% by weight of at least one surface active agent. The term "S/W/O" means a double emulsion in which polymer emulsion particles comprising polymer solids (S) (internal phase) emulsified in water (W) are present in oil (O) (i.e. external volatile hydrocarbon phase.). The content of the solid copolymer in the preparation is preferably within the range of from 2.5 to 25% by weight.

The preferable copolymer contained in the above-mentioned aqueous emulsion is derived from a monomer mixture of from 30 to 80% by weight of at least one acrylate selected from butyl acrylate, isobutyl acrylate, hexyl acrylates and 2-ethylhexyl acrylate and from 70 to 20% by weight of at least one methacrylate selected from methyl methacrylate, ethyl methacrylate and butyl methacrylate.

The humectants used in the present invention may be any of the humectants which are incorporated into conventional eye makeup preparations. Examples of such humectants are glycols, such as propylene glycol, hexylene glycol, 1,3-butylene glycol, dipropylene glycol, various polyethylene glycols presently marketed; glycerine and the like.

The pharmaceutically acceptable finely divided inorganic pigments used in the present invention may be any of the inorganic pigments which are incorporated into conventional eye makeup preparations. Examples of such inorganic pigments are various iron oxides, ultramarines, chromium oxide greens, chromium hydroxide greens, mica, talc, kaolin, titanium dioxide and the like.

The surface active agents used in the present invention may be any of the surface active agents which are incorporated into conventional eye makeup preparations. Examples of such surface active agents are: polysorbates; sorbitan esters, such as sorbitan dioleate, sorbitan laurate, sorbitan oleate, sorbitan palmitate, sorbitan sesquioleate, sorbitan sesquistearate and the like; triethanolamine stearate, triethanol amine palmitate, triethanolamine myristate and the like; monoglycerides; sodium salts of isobutylene and maleic anhydride copolymers, and the like.

The thickeners used in the present invention may be any of the thickeners which are incorporated into conventional eye makeup preparations. Examples of such thickeners are: various cellulose derivatives (e.g. MC, CMC, HEC and the like), polyvinyl alcohols, xanthan gums, magnesium aluminum silicates, hectorites, and; organically modified bentonites, organically modified hectorites and the like.

The plasticizers used in the present invention may be any of the plasticizers which are incorporated into conventional eye makeup preparations. Examples of such plasticizers are phthalates such as DBP and the like, citrates such as acetyl tributyl citrate, acetyl trioctyl citrate, triethyl citrate and the like.

The waxes, fats and oils used in the present invention may be any of the waxes, fats and oils which are incorporated into conventional eye makeup preparations. Examples of such waxes, fats and oils are: paraffin wax, carnauba wax, candelilla wax, bees wax, lanolin and lanolin derivatives, microcrystalline wax, ozokerite (or ceresine); spermaceti; squalane, isopropyl myristate, liquid paraffin and the like.

The volatile branched hydrocarbons used in the present invention may be any of those which have a boiling point within a range of from 150° to 220° C. Examples of such hydrocarbons are isoparaffinic hydrocarbons, such as Isopars available from Humble Oil & Refining Company, Soltrols available from Phillips Petroleum Co. and the like.

In addition to above-mentioned ingredients, the eye makeup preparations may contain optional ingredients, for example: preservatives, such as methyl-, ethyl-, propyl- and butyl-parabens, sodium dehydroacetate, sorbic acid, sodium benzoate and the like; perfumes, neutralizing agents, such as sodium bicarbonate, aqueous ammonia and the like; inorganic dispersing agents, such as sodium hexametaphosphate, sodium tripolyphosphate and the like; and the like.

The above mentioned various ingredients may be combined, under suitable stirring, in accordance with conventional procedures, to produce the desired eye makeup preparations. These eye makeup preparations can be easily applied onto, for example, the eyelids and the eyelashes with a hair pen or brush and exhibit highly desirable water-resistant, stain-proof and rub-proof properties. They can be removed, if desired, with conventional water-based eye makeup remover or soap and water, or with conventional oil-based makeup remover.

Although the incorporation of the aqueous copolymer emulsion specified above into eye makeup preparations has been described above, it should be noted that the aqueous copolymer emulsion can be also incorporated into other cosmetic preparations such as, for example, foundation makeup, body paint, artificial mole, stage makeup and the like.

EXAMPLES

The present invention now will be further illustrated by, but is by no means limited to, the following Examples.

SYNTHETIC EXAMPLE 1

A 500 ml, 4 neck flask was charged with 150 ml of water, and then, 3.0 g of polyoxyethylene lauryl ether and 0.3 g of lauryl sulfate were dissolved therein. A monomer mixture of 105 ml of butyl acrylate, 45 ml of methyl methacrylate and 2 ml of acrylic acid, and 10 ml of 10% by weight of an aqueous ammonium persulfate solution, were dropwise added into the flask. The contents of the flask were heated at a temperature of 70° to 80° C. The monomer mixture and the persulfate were separately added to the flask in many portions. The polymerization was carried out for 3 hours, under an agitation speed of 250 rpm (a torsion type stirrer was used). After the reaction mixture was agitated for a further 1 hour under heating, the unreacted monomer was removed under a reduced pressure of 500 mmHg. After cooling, the resultant mixture was dialyzed by a cellophane dialysis membrane, whereby ionic impurities were removed. A polymer emulsion having a good film-forming property was obtained.

SYNTHETIC EXAMPLES 2

A 500 ml, 4-neck separable flask was charged with 150 ml of water, and then, 4.5 g of polyoxyethylene lauryl ether and 0.2 g of lauryl sulfate were dissolved therein. A monomer mixture of 45 ml of butyl acrylate, 45 ml of 2-ethylhexyl acrylate, 60 ml of methyl methacrylate and 3 ml of acrylic acid, and 10 ml of 10% by weight of ammonium persulfate in a water solution were separately dropwise added to the flask in many portions. When the monomer mixture and the persulfate were added, the contents of the flask were heated at a temperature of 70° to 75° C. and agitated at a speed of 250 rpm (a torsion type stirrer was used). The polymerization was carried out for 3 hours. After completion of the polymerization, the reaction mixture was agitated for a further 1 hour under heating. Then, the reaction mixture was subject to deodorization under a reduced pressure of 500 mmHg. After cooling, the resultant mixture was dialyzed by a cellophane dialysis membrane, whereby ionic impurities were removed from the mixture. Thus, a polymer emulsion having a good film-forming property was obtained.

Various copolymer emulsions having the compositions shown in Table 1 below were prepared in the same manner as described in Synthetic Examples 1 and 2. The properties of the various copolymer emulsions were evaluated in accordance with the test procedure mentioned below and the results thereof are also shown in Table 1 below.

[Test Procedure]

1. Clarity (or transparency): A copolymer emulsion sample is coated on the skin and a clear glass plate to form films, each having a size of 50 mm×15 mm, and after drying, the clarity of the films is evaluated with the naked eye.

2. Tackiness: A copolymer emulsion sample is coated on the skin and a nylon plate having a size of 0.5×20×50 mm under the conditions of a temperature of 25° C. and a relative humidity of 50%, and after 30 minutes the stickiness of the films thus obtained is visually determined with a micro spatula.

3. Whitening Degree: A copolymer emulsion sample is coated on a nylon plate having a size of 0.5×20×50 mm, and after drying for 5 hours, the coated nylon plate is dipped in distilled water. The whitening and the swelling degree of the films are evaluated with the naked eye one day, three days and seven days after dipping.

4. Water resistant and adhesive property: Each sample film used in the above mentioned whitening degree test is evaluated with the naked eye with respect to the adhesion degree and the peeling degree thereof.

5. Dry adhesive property: A copolymer emulsion sample is coated on the skin and a nylon plate having a size of 0.5×20×50 mm under the conditions of a temperature of 25° C. and a relative humidity of 50%, and after 30 minutes, the adhesion properties of the films thus obtained are evaluated by peeling of the films from the surfaces with a micro spatula.

The results shown in Table 1 are evaluated according to the following rating standards.

Rating
5 ... Excellent
4 ... Good
3 ... Fair
2 ... Poor
1 ... Bad

TABLE 1

| Run No.*1 | Monomer Ratio*2 (by weight) | Tg*3 (calc.) (°C.) | Film forming property | | Water-resistant & adhesive property | | Dry adhesion |
|---|---|---|---|---|---|---|---|
| | | | Clarity | Tackiness | Whitening | water-resistant adhesive property | |
| 1 | BA/MMA 70/30 | −24.4 | 4 | 5 | 3 | 4 | 4 |
| 2 | BA/MMA 40/60 | 18.3 | 4 | 4 | 3 | 4 | 4 |
| 3 | BA/EMA 60/40 | −19.9 | 4 | 5 | 3 | 4 | 4 |
| 4 | BA/EMA 40/60 | 3.2 | 4 | 4 | 3 | 4 | 4 |
| 5 | BA/BMA 70/30 | −37.9 | 4 | 5 | 3 | 4 | 4 |
| 6 | BA/BMA 60/40 | −31.0 | 4 | 4 | 3 | 4 | 4 |
| 7 | 2EHA/MMA 70/30 | −18.9 | 4 | 5 | 4 | 4 | 4 |
| 8 | 2EHA/MMA 60/40 | −6.4 | 4 | 5 | 4 | 4 | 4 |
| 9 | 2EHA/EMA 60/40 | −15.0 | 4 | 5 | 4 | 4 | 4 |
| 10 | 2EHA/BMA 40/60 | −12.9 | 4 | 5 | 4 | 4 | 4 |
| 11 | BA/2EHA/MMA 40/40/20 | −33.1 | 4 | 5 | 4 | 5 | 4 |
| 12 | BA/2EHA/MMA 40/30/30 | −22.0 | 4 | 5 | 4 | 5 | 4 |
| 13 | BA/2EHA/MMA 30/30/40 | −9.0 | 4 | 5 | 4 | 5 | 4 |
| 14 | BA/2EHA/MMA 30/20/50 | 4.5 | 4 | 4 | 4 | 4 | 4 |
| 15 | BA/2EHA/EMA 40/30/30 | −27.8 | 4 | 5 | 4 | 5 | 4 |
| 16 | BA/2EHA/EMA 30/30/40 | −17.5 | 4 | 5 | 4 | 5 | 4 |
| 17 | BA/2EHA/EMA 30/20/50 | −7.1 | 4 | 5 | 4 | 5 | 4 |
| 18 | BA/2EHA/BMA 30/20/50 | −22.3 | 4 | 5 | 4 | 5 | 4 |
| 19 | BA/2EHA/BMA 20/20/60 | −14.5 | 4 | 5 | 4 | 5 | 4 |
| 20 | BA/2EHA/MMA/BMA 20/30/10/40 | −16.5 | 4 | 5 | 4 | 5 | 4 |
| 21 | EA/MMA 80/20 | −6.8 | 4 | 4 | 2 | 2 | 3 |
| 22 | EA/MMA 60/40 | 14.4 | 4 | 4 | 2 | 2 | 3 |
| 23 | EA/EMA 80/20 | −11.2 | 4 | 4 | 2 | 2 | 3 |
| 24 | EA/EMA 50/50 | 12.9 | 4 | 4 | 2 | 2 | 3 |
| 25 | EA/BMA 40/60 | 0.0 | 4 | 4 | 2 | 2 | 3 |
| 26 | EA/BA/BMA 20/20/60 | −8.4 | 4 | 4 | 2 | 2 | 3 |
| 27 | EA/BA/MMA 45/30/25 | −14.0 | 4 | 4 | 2 | 2 | 3 |

TABLE 1-continued

| Run No.[*1] | Monomer Ratio[*2] (by weight) | $T_g$[*3] (calc.) (°C.) | Film forming property | | Water-resistant & adhesive property | | Dry adhesion |
|---|---|---|---|---|---|---|---|
| | | | Clarity | Tackiness | Whitening | water-resistant adhesive property | |
| 28 | EA/2EHA/MMA 40/30/30 | −9.2 | 4 | 5 | 3 | 2 | 3 |

[*1] Run Nos. 21 to 28: Comparative Example
[*2] BA: Butyl acrylate
2EHA: 2-Ethylhexyl acrylate
EA: Ethyl acrylate
MMA: Methyl methacrylate
EMA: Ethyl methacrylate
BMA: Butyl methacrylate
[*3] $T_g$: Glass transition temperature (°C.)

EXAMPLE 1

By using various amounts of the copolymer emulsion derived from 40% by weight of butyl acrylate, 30% by weight of 2-ethylhexyl acrylate and 30% by weight of methyl methacrylate (see Run No. 12 in Table 1), aqueous and film-forming type eye makeup preparations A to G (i.e. eye liner) were prepared. The compositions and the properties of the makeup preparations are shown in Table 2 below. The content of the solid copolymer in the aqueous emulsion was 50% by weight.

As is clear from the results in Table 2, when 15% or more, preferably from 20% to 50%, by weight, of the aqueous emulsion is used, excellent results are obtained. Thus, it is epoch-making that the aqueous copolymer emulsion of the present invention can impart these excellent results to eye makeup preparations.

four samples were 50% by weight. The other ingredients incorporated into the sample were as follows.

| Ingredient | parts by weight |
|---|---|
| Carbon black | 3 |
| Black iron oxide | 5 |
| Titanium dioxide | 1 |
| Sodium polyphosphate | 0.05 |
| Deionized water | 35.95 |
| Polyoxyethylene sorbitan monooleate | 0.5 |
| Glycerin | 3 |
| Sodium carboxymethyl cellulose | 1 |
| Bentonite | 0.5 |
| Polymer emulsion (Solid content 50 wt. %) | 50 |
| Preservative | q.s. |
| Perfume | q.s. |

TABLE 2

| | Eye Makeup Preparations | | | | | | |
|---|---|---|---|---|---|---|---|
| | A | B | C | D | E | F | G |
| Composition | | | | | | | |
| Polymer Emulsion (Solid Content 50 wt. %) (BA/2EHA/MMA = 4/3/3) | 5 | 10 | 15 | 20 | 40 | 50 | 60 |
| Glycerin | 5 | 5 | 5 | 5 | 5 | 5 | 5 |
| Deionized water | 71.5 | 66.5 | 61.8 | 57.1 | 37.3 | 27.3 | 17.4 |
| P.O.E. sorbitan lauryl ester | 1 | 1 | 1 | 1 | 1 | 1 | 1 |
| Sodium carboxy methyl cellulose | 1 | 1 | 0.8 | 0.5 | 0.4 | 0.4 | 0.3 |
| Bentonite | 0.5 | 0.5 | 0.4 | 0.4 | 0.3 | 0.3 | 0.3 |
| Olive oil | 5 | 5 | 5 | 5 | 5 | 5 | 5 |
| Pigment (mixed lake) | 10 | 10 | 10 | 10 | 10 | 10 | 10 |
| Polyvinyl alcohol (partially saponified) | 1 | 1 | 1 | 1 | 1 | 1 | 1 |
| Properties of Product[*1] | | | | | | | |
| Film-forming property | 1 | 2 | 2 | 3 | 3 | 3 | 3 |
| Adhesive property (Tackiness) to skin | 1 | 1 | 2 | 3 | 3 | 3 | 3 |
| Water-resistance property | 1 | 1 | 2 | 3 | 3 | 3 | 3 |
| Oil resistance | 1 | 3 | 3 | 3 | 3 | 3 | 3 |
| Easy to remove cosmetics | 3 | 3 | 3 | 3 | 3 | 3 | 1[*2] |

[*1] Rating Standard:
3 ... Good or Excellent
2 ... Fair
1 ... Poor
[*2] The adhesive property (or tackiness) is too high.

EXAMPLE 2

By using an aqueous copolymer emulsion of 30% by weight of butyl acrylate, 30% by weight of 2-ethylhexyl acrylate and 40% by weight of methyl methacrylate prepared as mentioned above (see Run No. 13 of Table 1), an eye liner was prepared in order to evaluate the water-resistant, the stain-proof and the rub-proof properties of the eye liner according to the present invention. For comparison, eye liner samples A, B and C, each containing an aqueous copolymer emulsion having the composition shown in Table 3 below were also evaluated. The contents of the solid copolymers in the The test procedures were as follows.
(1) Practical Application Test
The samples were applied onto the skins of the eyelids of fifty women and the cosmetic properties of the samples were visually evaluated.
(2) Physical Test
Each sample eyeliner was coated on the surface of a nylon plate having a size of 10 mm×40 mm, and after drying the sample for 3 hours at a room temperature, the following tests were carried out. The results are shown in Table 3 below.

(i) Rub-proof adhesion property

The sample plate is charged into a 50 ml sample tube together with 10 g of polyacetal resin beads and the sample tube is shaken for 5 hours on a shaker. Thus, the abrasion degree of the coated film is evaluated.

(ii) Water-resistant and rub-proof adhesion property

The sample plate is charged into a 50 ml sample tube together with 10 g of polyacetal resin beads and 20 ml of deionized water, and the sample tube is shaken for 5 hours by a shaker. The adhesion property and the dissolution degree of the coated film are evaluated.

TABLE 3

| | Eye liner of this invention BA/2EHA/MMA = 30/30/40 | Comparative Sample A EA/BA/MMA = 40/30/30 | Comparative Sample B EA/MMA = 90/10 | Comparative Sample C EA/Styrene = 70/30 |
|---|---|---|---|---|
| Practical Application Test | | | | |
| Crack of film | 4 | 3 | 2 | 2 |
| Partial peeling of film | 4 | 3 | 2 | 3 |
| Sweat-proof property | 4 | 2 | 1 | 2 |
| Sebum-proof property | 4 | 4 | 4 | 4 |
| Physical Test | | | | |
| Rub-proof adhesion property | 4 | 4 | 3 | 3 |
| Water-resistant and Rub-proof Adhesion property | 4 | 2 | 1 | 1 |

(Remarks) Score Standard:
4 ... Good or Excellent
3 ... Fair
2 ... Poor
1 ... Bad The results in Table 3 clearly show the excellent effects of the present invention.

EXAMPLE 3

A liquid film forming type eye liner having the following composition was prepared as mentioned below.

[Composition]

| Ingredient | parts by weight |
|---|---|
| Carbon black | 3 |
| Black iron oxide | 5 |
| Titanium dioxide | 1 |
| Sodium polyphosphate | 0.05 |
| Deionized water | 35.95 |
| Polyoxyethylene sorbitan monooleate | 0.5 |
| Glycerin | 3 |
| Sodium carboxymethyl cellulose | 1 |
| Bentonite | 0.5 |
| Polymer emulsion (BA/2EHA/MMA = 40/30/30, Solid content 50 wt. %) | 50 |
| Preservative | q.s. |
| Perfume | q.s. |

[Procedure]

The sodium polyphosphate and the polyoxyethylene sorbitan monooleate were dissolved in the deionized water, and then, the carbon black, the black iron oxide and the titanium dioxide were dispersed therein. This mixture was homogeneously milled and dispersed by using a colloid mill. Into the dispersion thus obtained, the glycerin, the sodium carboxymethyl cellulose and the bentonite were added. While the mixture was agitated, the polymer emulsion, the preservative and the perfume were added, and the mixture was further mixed until a uniform mixture was obtained. Thus, a black, pell-off type eye liner was prepared.

EXAMPLE 4

A cream or paste type mascara having the following composition was prepared as mentioned below.

[Composition]

| Ingredients | Parts by weight |
|---|---|
| Beeswax | 3 |
| Solid paraffin wax | 3 |
| Stearic acid | 2.5 |
| Light liquid paraffin | 5 |
| Deionized water | 36.5 |
| Triethanol amine | 1 |
| Polyvinyl alcohol | 1 |
| Bentonite | 2 |
| Talc | 5 |
| Black iron oxide | 13 |
| Polymer emulsion (BA/EMA = 60/40, Solid Content 50 wt %) | 25 |
| Propylene glycol | 3 |
| Perfume | q.s. |
| Preservative | q.s. |

[Procedure]

The propylene glycol, triethanol amine, bentonite and polyvinyl alcohol were dispersed or dissolved in the deionized water. The pigments were uniformly dispersed in the mixture, and then, the mixture was heated at a temperature of 70° C. Into this heated mixture, the oil phase components, which were also heated, were gradually added with stirring and were uniformly emulsified therein. After the emulsification, the polymer emulsion was added and uniformly mixed with the mixture. Then, the preservative and perfume were added to the mixture and the mixture was cooled to 40° C. Thus, a black, cream or paste type mascara was prepared.

EXAMPLE 5

An S/W/O paste type mascara having the following composition was prepared.

| Ingredient | Parts by weight |
|---|---|
| [Oil phase] | |
| Volatile branched hydrocarbon (Isopar H) | 30 |
| Solid paraffin wax | 8 |
| Lanolin derivatives | 8 |
| Sorbitan monopalmitate | 4 |
| Black iron oxide | 10 |
| [Water Phase] | |
| Copolymer emulsion (BA/2EHA/MMA = 30/30/40, | 30 |

| Ingredient | Parts by weight |
| --- | --- |
| solid content 50 wt. %) | |
| Deionized water | 10 |
| Preservative | q.s. |
| Perfume | q.s. |

[Procedure]

The oil phase was heated at a temperature of 70° C. with stirring to thereby form a homogeneous phase. The water phase was heated to a temperature of 70° C. and, then, added to the oil phase. The emulsified mixture thus obtained was cooled. Thus, black mascara was obtained.

What we claim is:

1. In an aqueous dispersion type eye makeup preparation comprising from 20 to 50% by weight of a film forming agent, from 1 to 10% by weight of at least one humectant, from 5 to 30% by weight of at least one pharmaceutically acceptable finely divided inorganic pigment, from 0.1 to 5% by weight of at least one surface active agent, from 0.1 to 3% by weight of at least one thickener, from 0.5 to 5% by weight of at least one plasticizer and a balance of water; wherein the improvement comprises that said film forming agent consists essentially of an aqueous emulsion of at least one member selected from the group consisting of copolymers derived from monomer mixtures of 30 to 80% by weight, of at least one alkyl acrylate having from $C_4$ to $C_{18}$ alkyl groups in the ester portion and 70 to 20% by weight of at least one alkyl methacrylate having from $C_1$ to $C_4$ alkyl groups in the ester portion.

2. An eye makeup preparation as claimed in claim 1, wherein said alkyl methacrylate is selected from the group consisting of methyl methacrylate, ethyl methacrylate and butyl methacrylate.

3. An eye makeup preparation as claimed in claim 1, wherein said alkyl acrylate is selected from the group consisting of butyl acrylate, isobutyl acrylate, hexyl acrylates and 2-ethylhexyl acrylate.

4. An eye makeup preparation as claimed in claim 3, wherein said alkyl acrylate is 2-ethylhexyl acrylate or any mixture thereof with the other alkyl acrylates having from $C_4$ to $C_8$ alkyl groups.

5. An eye makeup preparation as claimed in claim 1, wherein the amount of said aqueous emulsion is within the range of from 20 to 50% by weight, based on the total weight of the makeup preparation.

6. An eye makeup preparation as claimed in claim 5, wherein the content of said copolymer in solid is within the range of from 10 to 25% by weight, based on the total weight of said preparation.

7. In an O/W emulsion type eye makeup preparation comprising from 20 to 50% by weight of a film forming agent, from 1 to 30% by weight of at least one member selected from waxes, fats and oils, from 1 to 10% by weight of at least one humectant, from 5 to 30% by weight of at least one pharmaceutically acceptable finely divided inorganic pigment, from 0.1 to 5% by weight of at least one surface active agent, from 0.1 to 3% by weight of at least one thickener and from 20 to 50% by weight of water; wherein the improvement comprises that said film forming agent consists essentially of an aqueous emulsion of at least one member selected from the group consisting of copolymers derived from monomer mixtures of 30 to 80% by weight of at least one alkyl acrylate having from $C_4$ to $C_{18}$ alkyl groups in the ester portion and 70 to 20% by weight of at least one alkyl methacrylate having from $C_1$ to $C_4$ alkyl groups in the ester portion.

8. An eye makeup preparation as claimed in claim 7, wherein said alkyl methacrylate is selected from the group consisting of methyl methacrylate, ethyl methacrylate and butyl methacrylate.

9. An eye makeup preparation as claimed in claim 7, wherein said alkyl acrylate is selected from the group consisting of butyl acrylate, isobutyl acrylate, hexyl acrylate and 2-ethylhexyl acrylate.

10. An eye makeup preparation as claimed in claim 9, wherein said alkyl acrylate is 2-ethylhexyl acrylate or a mixture thereof with at least one other alkyl acrylate having from $C_4$ to $C_8$ alkyl groups.

11. An eye makeup preparation as claimed in claim 7, wherein the content of said copolymer in solid form is within the range of from 10 to 25% by weight, based on the total weight of said preparation.

* * * * *